United States Patent [19]

Riedl et al.

[11] Patent Number: 5,399,355
[45] Date of Patent: Mar. 21, 1995

[54] AGENT FOR TRANSDERMAL ADMINISTRATION CONTAINING ERGOLINE DERIVATIVES

[75] Inventors: Jutta Riedl; Clements Günther; Ralph Lipp, all of Berlin, Germany

[73] Assignee: Schering Aktiengesellschaft, Berlin and Bergkamen, Germany

[21] Appl. No.: 40,393

[22] Filed: Mar. 30, 1993

Related U.S. Application Data

[63] Continuation of Ser. No. 884,083, May 18, 1992, abandoned.

[30] Foreign Application Priority Data

May 18, 1991 [DE] Germany ............... 41 16 912.3

[51] Int. Cl.$^6$ ............................................. A61F 13/00
[52] U.S. Cl. ................... 424/448; 424/447; 424/449
[58] Field of Search ............ 424/447, 448; 514/449, 514/946–947

[56] References Cited

U.S. PATENT DOCUMENTS

| | | | |
|---|---|---|---|
| 4,692,452 | 9/1987 | Cerny et al. ................. | 514/288 |
| 4,782,063 | 11/1988 | Garbrecht et al. ................. | 546/69 |
| 4,835,159 | 5/1989 | Garbrecht et al. ................. | 546/69 |
| 4,883,669 | 11/1989 | Chien et al. ................. | 424/449 |
| 5,071,657 | 12/1991 | Oloff et al. ................. | 424/486 |
| 5,229,129 | 7/1993 | Chiang ................. | 424/449 |

FOREIGN PATENT DOCUMENTS

| | | |
|---|---|---|
| 137278 | 4/1985 | European Pat. Off. . |
| 155229 | 9/1985 | European Pat. Off. . |
| 2146526 | 4/1985 | United Kingdom . |
| 91/00746 | 7/1989 | WIPO . |

OTHER PUBLICATIONS

Embase N. 92118765. "Future treatment of Parkinson'-disease".

"Permeation enhancers . . . delivery systems" on pharmaceutical Technology pp. 132–141 (1990).

*Primary Examiner*—Thurman K. Page
*Assistant Examiner*—Jyothsna Venkat
*Attorney, Agent, or Firm*—Millen, White, Zelano & Branigan

[57] ABSTRACT

An agent for transdermal administration contains ergoline derivatives optionally in combination with one or more penetration-enhancing agent or agents.

13 Claims, No Drawings

AGENT FOR TRANSDERMAL ADMINISTRATION CONTAINING ERGOLINE DERIVATIVES

This application is a continuation of application Ser. No. 07/884,083, filed May 18, 1992, now abandoned.

SUMMARY OF THE INVENTION

This invention relates to an agent for transdermal administration characterized in that it contains ergoline derivatives optionally in combination with one or more penetration-enhancing agents.

Ergoline derivatives, such as lisuride [3-(9,10-dihydro-6-methyl-8α-ergolinyl-1,1-diethylurea], already known since 1960, and its derivatives, which are described, i.a., in DE-A 2 238 540, EP-A 0021206, EP-A 0056358 and EP-A 0160840, are pharmacologically effective substances, which can be used for the production of pharmaceutical agents.

Such ergoline derivatives are, for example, those of general formula

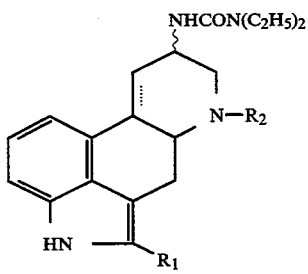

in which:
= symbolizes a single bond or a double bond,
$R_1$ represents a hydrogen atom, a halogen atom or an alkylthio group with 1 to 4 carbon atoms in an alkyl radical and
$R_2$ means an alkyl group with 1 to 4 carbon atoms, or its salt with a physiologically acceptable acid.

As highly effective ergoline derivatives, in addition to lisuride, the bromolisuride [=3-(2-bromo-9,10-dehydro-6-methyl-8α-ergolinyl-1,1-diethylurea], terguride [=3-(6-methyl-8α-ergolinyl-1,1-diethylurea] and proterguride [=3-(6-propyl-8α-ergolinyl)-1,1-diethylurea] can be mentioned as non-limiting examples.

As salts of these ergoline derivatives, the sulfates, phosphates, maleates, citrates or succinates can be mentioned as non-limiting examples.

As dopaminergic agonists, ergoline derivatives now have a secure place in the treatment of the most varied diseases, which are caused by hyperprolactinemia or in which prolactin is of pathogenetic importance.

For primary and secondary ablactation, dopaminergic agonists are the agents of choice, also for the fertility disorders of the female accompanying hyperprolactinemia. Also, the potency disorders of the male caused by hyper-prolactinemia can be treated successfully. While dopamine and dopaminergic agonists with healthy individuals stimulate the secretion of STH, they have the opposite effect in acromegalia. Premenstrual syndrome, preeclampsia, geriatrics, mastodynia are also associated with the wide spectrum of activity of prolactin and can be treated with dopaminergic agonists. Parkinson's disease is based on a dopamine deficiency, therefore Parkinson patients can be treated successfully with dopaminergic agonists.

Many ergoline derivatives, such as, for example, lisuride itself, have only a short terminal half-life, and it is consequently difficult over a prolonged period to attain constant plasma levels of the medicine in the blood.

It has now been found that ergoline derivatives such as those mentioned above and below optionally in combination with one or more penetration-enhancing agents can be used very well for the production of an agent for the transdermal administration of the active ingredient.

As is generally known, pharmaceutical agents to be administered transdermally have the advantage that they make possible a more uniform release of the active ingredient over a prolonged period, than generally is possible with other agents to be administered—for example, orally. These properties can advantageously be used in treating a number of diseases. But for poorly soluble active ingredients in usual plaster materials, such as for example, the ergoline derivatives, it is generally quite problematical to make transdermal systems which assure a penetration of the active ingredient through the skin that is sufficient for treatment.

It has now been found that it is surprisingly possible, with the help of the invention, to achieve a therapeutically sufficient and very uniform rate of penetration of the ergoline derivatives through the skin.

For production of pharmaceutical preparations, the active ingredient can be dissolved or suspended in suitable volatile solvents and/or penetration-enhancing agents. The obtained solutions or suspensions can be mixed with the usual auxiliary agents, such as, for example, thickeners. Solutions or suspensions according to the invention can be processed, for example, by silicone elastomers to plasters or bandages containing active ingredients (DE-A 31 31 610; U.S. Pat. No. 3,996,934 or U.S. Pat. No. 4,336,243).

Suitable volatile solvents are, for example, lower alcohols, ketones or lower carboxylic acid esters, such as ethanol, isopropanol, acetone or ethyl acetate, polar ethers, such as tetrahydrofuran, lower hydrocarbons, such as cyclohexane or benzin or else halogenated hydrocarbons, such as dichloromethane, trichloromethane, trichlorotrifluoroethane and trichlorofluoromethane. Also mixtures of these solvents are suitable.

Suitable penetration-enhancing agents are, for example, liquid, monovalent or multivalent aliphatic, cycloaliphatic or aromatic-aliphatic alcohols with up to 8 carbon atoms, such as 1,2-propanediol, menthol, dexpanthenol or benzyl alcohol, saturated and unsaturated fatty alcohols with 8 to 18 carbon atoms, such as lauryl alcohol, isocetyl alcohol or cetyl alcohol, hydrocarbons, such as mineral oil, saturated and unsaturated fatty acids with 8 to 18 carbon atoms, such aslauric acid, isopalmitic acid, isostearic acid or oleic acid, fatty acid esters of general formula $$CH_3-(CH_2)_n-COOR$$

in which:
n means a number from 2 to 18 and
R means an alkyl radical with a maximum of 6 carbon atoms, or dicarboxylic acid diester of general formula $$R'OCO(CH_2)_mCOOR'$$

in which:
m means a number from 4 to 8 and
R' means respectively an alkyl radical with a maximum of 6 carbon atoms. Fatty acid esters, which are suitable for the agent according to the invention, are, for example, those of lauric acid, myristic acid, stearic acid and palmitic acid, such as, for example, the methyl ester, ethyl ester, 2-hydroxyethyl ester, glycerol ester, propyl ester, isopropyl ester, butyl ester, sec-butyl ester or isobutyl ester of these acids. Especially preferred esters are those of palmitic acid, isopalmitic acid, isostearic acid and stearic acid, especially for production of lisuride-containing agents for transdermal administration, such as their methyl ester and especially their isopropyl ester. Suitable dicarboxylic acid diesters are, for example, the diisopropyladipate, diisobutyladipate and diisopropylsebacate. There is no need for a more detailed explanation that also mixtures of these penetration-enhancing agents are suitable for the production of the agent according to the invention.

A very uniform administration with adjusted dosage of the active ingredient can be achieved if the active ingredient is embedded in a transdermal therapeutic system (TTS). Suitable transdermal therapeutic systems are those which are usually used for percutaneous administration of active ingredients (Yie W. Chien: "Transdermal Controlled Systemic Medications," Marcel Dekker, Inc., New York and Basel, 1987, Dr. Richard Baker: "Analysis of Transdermal Drug Delivery Patents 1934 to 1984" and "Analysis of Recent Transdermal Delivery Patents, 1984–1986 and Enhancers" Membrane Technology & Research 1030 Hamilton Court, Menlo Park, Calif. 94025 (415) 328–2228).

Thus, for example, a transdermal therapeutic system can be used which comprises:

a) an impermeable covering layer,
a pharmaceutical agent layer permeable for these components adhering to the covering layer, containing the ergoline derivative and optionally the penetration-enhancing agent or agents, a pharmaceutical agent layer which is self-adhesive or is covered over or surrounded by a skin contact adhesive, which also can contain a penetration-enhancing agent and
a removable protective layer, or
b) an impermeable covering layer,
a pharmaceutical agent reservoir on or in the covering layer, optionally containing penetration-enhancing agents for the ergoline derivative,
a permeable polymer layer for these components,
a permeable skin contact adhesive layer containing optionally a penetration-enhancing agent and
a removable protective layer.

A transdermal therapeutic system according to variant a) represents a simple matrix system. It can be produced, for example, as follows.

A solution or suspension of 1 to 25% by weight of active ingredient, 0–40% by weight of a penetration-enhancing agent, 30–70% by weight of a medicinally usual adhesive filled with a suitable volatile solvent to 100% by weight is painted on a plane, impermeable covering layer and after the drying provided with a removable protective layer.

If a medicinally usual matrix former is used which, after the drying of the system, does not adhere or insufficiently adheres to the skin, the system can be covered over or surrounded in addition with a skin contact adhesive before the application of the removable protective layer.

Suitable solvents and penetration-enhancing agents are, for example, the already mentioned liquids of this type. As medicinally usual adhesives, for example, polyacrylates, silicones, polyurethanes, as well as natural or synthetic rubbers are suitable. As other matrix formers, cellulose ether, polyvinyl compounds or silicates are suitable.

As protective layers, all sheets which are usually used in transdermal therapeutic systems are suitable. Such sheets are, for example, siliconized or coated with fluoropolymers.

As a covering layer in this system, for example, 10 to 100 $\mu$m thick sheets of polyethylene or polyester can be used selectively pigmented or metallized. The pharmaceutical agent layer applied on it preferably has a thickness of 20 to 500 $\mu$m. The dispensing of the active ingredients takes place preferably on an area of 5 to 100 cm$^2$.

A transdermal therapeutic system according to variant b) above can be produced, for example, as follows.

An impermeable sheet is deformed by heat and/or traction, so that a bulge holding 0.1 to 3 ml results. This is filled with an active ingredient-containing solution or suspension containing 1–50% by weight of active ingredient in a penetration-enhancing agent. The active ingredient-containing solution or suspension can also be thickened with up to 10% by weight of matrix former.

As a covering for the reservoir on the skin side, a welded or bonded permeable polymer layer is used, on which a permeable skin contact adhesive layer and a removable protective layer are applied.

In this system, the above-mentioned penetration-enhancing agents can be used. As a permeable polymer layer, for example, a 20 to 200 $\mu$m thick sheet of cellulose esters, cellulose ethers, silicones or polyolefin compounds is used. By variation of this polymer layer (e.g., composition and thickness), the rate of diffusion of the active ingredient or active ingredient mixture can be routinely varied within wide limits.

As an adhesive and protective layer, the same materials are suitable which are described in the transdermal therapeutic system according to variant a).

Thus, by simple routine variation of the various parameters, transdermal therapeutic systems with different release rates of the active ingredient or active ingredient mixture can be produced, which can be packaged for the purpose of storage, for example, in aluminum foil.

The concentration, in which the ergoline derivative is optimally dissolved or suspended, e.g., in the penetration enhancer is, of course, dependent on the type of the active ingredient and penetration enhancer used and the desired single dose. It is determined in the individual case routinely by preliminary tests familiar to one skilled in the art, such as, for example, the determination of achievable blood plasma concentrations of active ingredient per area in selected agents according to the invention. In general, active ingredient concentrations of 0.2 to 20% by weight of the agent according to the invention will be sufficient.

The determination of the extent of the speed of the percutaneous resorption by the agent according to the invention can take place, for example, by radioactively-labeled ergoline derivatives.

Freshly prepared skin, freed from subcutaneous fat, from the abdomen of hairless mice is clamped in a Franz diffusion cell, which as a collecting liquid contains isotonic polyethylene glycol-(MG 400) solution or phosphate buffer solution of pH 7. Then, 2 $\mu$l of test solution is added on the skin and the content of the ergoline derivative reaching the collecting liquid is determined after 24, 48 and 72 hours by liquid scintillation counting.

A 5% by weight solution of ergoline in propylene glycol (PG) and propylene glycol-lauric acid 9:1 w/w (PG+10% LA) was tested.

The following table shows the results obtained in this test:

TABLE

| Parameter | Dimension | Lisuride in PG + 10% LA | |
|---|---|---|---|
| maximum flow | µg/cm²/h | 4.0 | 14.6 |
| t (maximum flow) | h | 15.1 | 4.5 |
| average flow (0–24 hours) | µg/cm²/h | 3.0 | 7.0 |
| average flow (24–48 hours) | µg/cm²/h | 1.6 | 4.3 |
| dose | µg/10 µl | 477 | 469 |
| dose resorbed in 48 hours | µg | 75.4 | 183.0 |
| dose resorbed in 48 hours | % | 15.8 | 39.0 |

The therapeutic plasma level ($C_{ss}$) for the treatment of Parkinson's disease is about 1–2 ng/ml, in the other indications mentioned herein, the therapeutic plasma level is lower.

Percutaneous flow (I), which for a given surface (A) is necessary to attain the therapeutic plasma level, can be calculated from the total body clearance (CL) of LISURIDE as follows:

$$I = \frac{CL * C_{SS}}{A}$$

If a value of 50 cm² is selected for a TTS, the desired therapeutic plasma level of 1–2 ng/ml is achieved at a total clearance for LISURIDE of 65250 ml/h with a percutaneous flow of 1.3–2.7 µg/cm²/h. The flows achieved in vitro through mouse skin of up to over 14 µg/cm²/h are clearly above this requirement. Also, in a realistic assumption of a permeability of the mouse skin for lisuride being higher than human skin by the factor 5, the necessary transdermal flow with humans will be achieved.

The agents for transdermal administration containing ergoline derivatives according to the invention can be used to treat the same diseases, as the previously known agents to be administered, for example, orally or subcutaneously, which contain ergoline derivatives. They are administered transdermally analogously to transdermal systemic administration of other agents such as described in the references cited herein.

This invention is significant since orally administered ergoline derivatives, such as lisuride, undergo a high and individually greatly dispersing deactivation during the first liver passage. Moreover, in most cases, they have a short biological half-life. Consequently, it is not possible by one-time oral administration to achieve constant, therapeutically effective plasma levels in the blood over a prolonged period. In contrast, with a TTS, continuous dispensing of active ingredients can be achieved over a period of several days.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German Application P 41 16 912.3, filed May 18, 1991, are hereby incorporated by reference.

EXAMPLES

The following materials were used to prepare the systems shown in the examples:

Polyester sheets of a 0.074 mm thickness (Scotch-Pak ® 1009) of the manufacturer 3M; polypropylene sheet (Celgard ® 2500) of the manufacturer Celanese, liner sheet ScotchPak ® 1022 and 1360 of the manufacturer 3M; transfer adhesive 9871 of the manufacturer 3M; polyacrylester adhesive of type Gelva ® 2723 of the manufacturer Monsanto and silicone adhesive of the type X-7-4502 of the manufacturer Dow Corning.

EXAMPLE 1

In 100 g of a 50% solution of silicone adhesive in benzin,
2.0 g of lisuride and
10.0 g of isopropylpalmitate are dissolved or suspended in succession with stirring (since the adhesives are cloudy, it cannot be definitely decided whether a complete solution is present). After degassing the batch over 24 hours, the solution/suspension is applied by a knife-over-roll coating device on a fluoropolymer-coated polyester sheet so that, after removal of the volatile solvent at 60°–80° C., a uniform film of 100 g/m² of solid coating results. Then, it is laminated with an opaque polyester covering sheet. The thus obtained laminate is divided by a cutting device into individual plasters of a 10 cm² area and packaged airtight in an aluminized bag. After removal of the liner sheet, the plaster adheres to the skin.

The determination of the content yields a uniform active ingredient distribution of 4.4 mg/cm² on the average.

EXAMPLE 2

In 100 g of a 50% solution of polyacrylate adhesive in ethyl acetate,
1.0 g of lisuride and
17.5 g of 1,2-propanediol
are dissolved or suspended in succession with stirring. After degassing the batch over 24 hours, the solution/suspension is applied by a knife-over-roll coating device on a polyester sheet so that, after removal of the volatile solvent at 60°–80° C., a uniform film of 50 g/m² of solid coating results. Then, it is laminated with an opaque polyester covering sheet. The thus obtained laminate is divided by a cutting device into individual plasters of a 10 cm² area and packaged airtight in an aluminized bag. After removal of the liner sheet, the plaster adheres to the skin.

The content of ergoline derivative is 1.1 mg/cm² on the average.

EXAMPLE 3

In 100 g of a 50% solution of polyacrylate adhesive in ethyl acetate,
1.0 g of terguride
1.0 g of highly dispersed silicic acid and
17.5 g of 1,2-propanediol with 10% 1-dodecanol are dissolved or suspended in succession with stirring.

After degassing the batch over 24 hours, the solution/suspension is applied by a knife-over-roll coating device on a siliconized polyester liner so that, after removal of the volatile solvent at 60°–80° C., a uniform film of 100 g/m² of solid coating results. Then, it is laminated with an opaque polyester covering sheet. The thus obtained laminate is divided by a cutting device into individual plasters of a 10 cm² area and packaged airtight in an aluminized bag. After removal of the liner sheet, the plaster adheres to the skin.

The content of terguride is at 2.2 mg/cm² each.

EXAMPLE 4

An opaque polyester sheet of a 7.4 cm diameter is deformed by heat and traction, so that a round bulge of a 10 cm² area results. This is filled with 1 ml of a suspension of 3.0 mg of proterguride in 1,2-propanediol, which contains 10% dexpanthenol. A polypropylene sheet is welded on the edge. Depending on the pressure per time unit, the sealing temperature is between 70° C. and 100° C. A contact adhesive sheet is transferred to the permeable polymer layer. The plaster is provided with a liner and packaged airtight in an aluminized bag.

What is claimed is:

1. A transdermal therapeutic system which comprises:
   a) an impermeable covering layer;
   adhering to the covering layer, a permeable pharmaceutical agent layer comprising an ergoline derivative selected from the group consisting of 2-bromolisuride, terguride, proterguride and physiologically acceptable acid salts thereof, a pharmaceutically acceptable carrier effective for transdermal administration and, optionally, a transdermally effective penetration-enhancing agent,
   wherein the pharmaceutical agent layer contains a polyacrylate skin contact adhesive such that it is self-adhesive or is covered over or surrounded by a polyacrylate skin contact adhesive, which can optionally contain penetration-enhancing agents;
   and a removable protective layer, or
   b) an impermeable covering layer,
   a pharmaceutical agent reservoir on or in the covering layer, comprising an ergoline derivative selected from the group consisting of 2-bromolisuride, terguride, proterguride and physiologically acceptable acid salts thereof, a pharmaceutically acceptable carrier effective for transdermal administration and, optionally, a transdermally effective penetration-enhancing agent;
   a polymeric layer permeable for the components of the pharmaceutical agent reservoir;
   a permeable polyacrylate skin contact adhesive layer optionally containing penetration-enhancing agents; and
   a removable protective layer.

2. The transdermal therapeutic system of claim 1, which comprises a penetration-enhancing agent.

3. The transdermal therapeutic system of claim 1, which comprises a penetration-enhancing agent.

4. The transdermal therapeutic system of claim 2, wherein the penetration-enhancing agent is 1,2-propanediol, menthol, dexpanthenol, benzyl alcohol, lauryl alcohol, isocetyl alcohol, cetyl alcohol, mineral oil, lauric acid, isopalmitic acid, isostearic acid, oleic acid, a fatty acid ester of the formula $$CH_3-(CH_2)_n-COOR$$

in which:
n is 2–18,
R is alkyl of up to 6 carbon atoms, or a dicarboxylic acid diester of the formula $$R'OCO(CH_2)_mCOOR'$$

in which:
m is 4 to 8 and
R' is alkyl of up to 6 carbon atoms.

5. The transdermal therapeutic system of claim 2, wherein the penetration-enhancing agent is propylene glycol, lauryl alcohol, lauric acid or mixtures thereof.

6. The transdermal therapeutic system of claim 2, wherein the penetration-enhancing agent is a mixture of propylene glycol and lauric acid in a weight ratio of 9:1.

7. The transdermal therapeutic system of claim 2, wherein the penetration-enhancing agent is a mixture of propylene glycol and lauryl alcohol.

8. The transdermal therapeutic system of claim 2, wherein the penetration-enhancing agent is 1,2-propanediol, menthol, dexpanthenol, benzyl alcohol, lauryl alcohol, isocetyl alcohol, cetyl alcohol, mineral oil, lauric acid, isopalmitic acid, isostearic acid, oleic acid, or a dicarboxylic acid diester of the formula $$R'OCO(CH_2)_mCOOR'$$

in which:
m is 4 to 8 and
R' is alkyl of up to 6 carbon atoms.

9. A transdermal therapeutic system which comprises:
   a) an impermeable covering layer;
   adhering to the covering layer, a permeable pharmaceutical agent layer comprising an ergoline derivative, selected from the group consisting of 2-bromolisuride, terguride, proterguride and physiologically acceptable acid salts thereof, a pharmaceutically acceptable carrier effective for transdermal administration and a transdermally effective penetration-enhancing agent,
   wherein the pharmaceutical agent layer contains a skin contact adhesive such that it is self-adhesive or is covered over or surrounded by a skin contact adhesive, which can, optionally, contain penetration-enhancing agents;
   and a removable protective layer, or
   b) an impermeable covering layer,
   a pharmaceutical agent reservoir on or in the covering layer, comprising an ergoline derivative selected from the group consisting of 2-bromolisuride, terguride, proterguride and physiologically acceptable acid salts thereof, a pharmaceutically acceptable carrier effective for transdermal administration and a transdermally effective penetration-enhancing agent;
   a polymeric layer permeable for the components of the pharmaceutical agent reservoir;
   a permeable skin contact adhesive layer containing penetration-enhancing agents; and
   a removable protective layer, wherein the penetration-enhancing agent is 1,2-propanediol, menthol, dexpanthenol, benzyl alcohol, lauryl alcohol, isocetyl alcohol, cetyl alcohol, mineral oil, lauric acid, isopalmitic acid, isostearic acid, oleic acid, or a dicarboxylic acid diester of the formula R'OCO(CH$_2$)$_m$COOR' in which:
m is 4 to 8 and
R' is alkyl of up to 6 carbon atoms.

10. The transdermal therapeutic system of claim 7, wherein the penetration-enhancing agent is propylene glycol, lauryl alcohol, lauric acid or mixtures thereof.

11. The transdermal therapeutic system of claim 9, wherein the penetration-enhancing agent is a mixture of propylene glycol and lauric acid in a weight ratio of 9:1.

12. The transdermal therapeutic system of claim 9, wherein the penetration-enhancing agent is a mixture of propylene glycol and lauryl alcohol.

13. The transdermal therapeutic system of claim 9, wherein the skin contact adhesive is a polyacrylate adhesive.

* * * * *